(12) United States Patent
Parfenova et al.

(10) Patent No.: US 9,095,307 B2
(45) Date of Patent: Aug. 4, 2015

(54) METHODS FOR DETECTION OF RESPIRATORY EFFORT AND SLEEP APNEA MONITORING DEVICES

(71) Applicant: Somnarus Inc., Mountain View, CA (US)

(72) Inventors: Maria A. Parfenova, Mountain View, CA (US); Alexandr S. Parfenov, Moscow (RU); Yuri P. Zobnin, Moscow (RU)

(73) Assignee: Somnarus Inc., Mountain View, CA (US)

( * ) Notice: Subject to any disclaimer, the term of this patent is extended or adjusted under 35 U.S.C. 154(b) by 0 days.

(21) Appl. No.: 14/213,712

(22) Filed: Mar. 14, 2014

(65) Prior Publication Data
US 2014/0213913 A1    Jul. 31, 2014

Related U.S. Application Data

(62) Division of application No. 13/830,736, filed on Mar. 14, 2013, now Pat. No. 8,740,806.

(60) Provisional application No. 61/723,682, filed on Nov. 7, 2012.

(51) Int. Cl.
*A61B 5/0205* (2006.01)
*A61B 5/00* (2006.01)
(Continued)

(52) U.S. Cl.
CPC ............ *A61B 5/4818* (2013.01); *A61B 5/0205* (2013.01); *A61B 5/02007* (2013.01);
(Continued)

(58) Field of Classification Search
CPC ............ A61B 5/4818; A61B 5/02007; A61B 5/0295; A61B 5/7257; A61B 5/14551; A61B 5/0205; A61B 5/725; A61B 5/6819

USPC .............................................. 60/323, 324, 340
See application file for complete search history.

(56) References Cited

U.S. PATENT DOCUMENTS 4,759,369 A * 7/1988 Taylor ........................ 600/323
4,860,766 A    8/1989 Sackner
(Continued)

FOREIGN PATENT DOCUMENTS

EP        2486850 A3     9/2012
WO    2005065540 A1     7/2005

OTHER PUBLICATIONS

Accutest SleepStrip brochure, dated Oct. 24, 2004, 2 pages (accessed Mar. 13, 2013).
(Continued)

*Primary Examiner* — Patricia Mallari
*Assistant Examiner* — Michael Catina
(74) *Attorney, Agent, or Firm* — Edward B. Weller

(57) ABSTRACT

A sleep apnea diagnostic system includes a housing that is configured to be attached to near the nose of a patient's face to sense physiological information of a patient. The housing includes sensors to sense the physiological information. The physiological information may be, for example, air flow through the nose or the mouth or both. The physiological information further may be, for example, blood volume. The sleep apnea diagnostic system includes at least one processor in the housing or external to the housing or both to analyze the physiological information to determine whether the patient has experienced irregular or abnormal respiratory activity and to detect respiratory effort. The analysis may be real time or delayed.

20 Claims, 13 Drawing Sheets

(51) Int. Cl.
  *A61B 5/1455* (2006.01)
  *A61B 5/02* (2006.01)
  *A61B 5/0295* (2006.01)

(52) U.S. Cl.
  CPC ........... *A61B5/0295* (2013.01); *A61B 5/14551* (2013.01); *A61B 5/725* (2013.01); *A61B 5/7257* (2013.01); *A61B 5/6819* (2013.01)

(56) References Cited

U.S. PATENT DOCUMENTS

| | | | |
|---|---|---|---|
| H0001039 H | * | 4/1992 | Tripp et al. ............. 128/206.28 |
| 6,368,287 B1 | | 4/2002 | Hadas |
| 6,811,538 B2 | | 11/2004 | Westbrook et al. |
| 7,024,235 B2 | | 4/2006 | Melker et al. |
| 7,066,180 B2 | | 6/2006 | Aylsworth et al. |
| 7,297,119 B2 | | 11/2007 | Westbrook et al. |
| 7,690,378 B1 | | 4/2010 | Turcott |
| 7,691,067 B2 | | 4/2010 | Westbrook et al. |
| 7,785,262 B2 | | 8/2010 | Melker et al. |
| 7,828,739 B2 | | 11/2010 | Arnold |
| 8,103,483 B2 | | 1/2012 | Lo et al. |
| 8,202,223 B2 | | 6/2012 | Cho et al. |
| 8,365,730 B2 | | 2/2013 | Baker, Jr. et al. |
| 2004/0059236 A1 | | 3/2004 | Margulies et al. |
| 2004/0260186 A1 | | 12/2004 | Dekker |
| 2005/0222502 A1 | | 10/2005 | Cooper |
| 2007/0027375 A1 | * | 2/2007 | Melker et al. ............. 600/340 |
| 2007/0208269 A1 | * | 9/2007 | Mumford et al. ............ 600/546 |
| 2008/0066753 A1 | * | 3/2008 | Martin et al. ............ 128/204.23 |
| 2009/0043179 A1 | | 2/2009 | Melker et al. |
| 2009/0069646 A1 | | 3/2009 | Yamamori et al. |
| 2009/0326402 A1 | | 12/2009 | Addison et al. |
| 2010/0016739 A1 | | 1/2010 | Shelley et al. |
| 2010/0121207 A1 | | 5/2010 | Moersdorf et al. |
| 2010/0152560 A1 | | 6/2010 | Turcott |
| 2010/0191128 A1 | | 7/2010 | Shelley et al. |
| 2011/0218409 A1 | | 9/2011 | Kugler et al. |
| 2011/0224498 A1 | | 9/2011 | Banet et al. |
| 2012/0190998 A1 | | 7/2012 | Armitstead et al. |
| 2014/0005557 A1 | | 1/2014 | Rich et al. |
| 2014/0094669 A1 | * | 4/2014 | Jaffe et al. ............. 600/324 |

OTHER PUBLICATIONS

Accutest SleepStrip Technical Information webpage, copyright 2013, http://www.accutest.net/products/sleepstrip-tech.php, (accessed Mar. 13, 2013).
Watermark ARES webpage, http://www.watermarkmedical.comlabout_ares.php, 2 pp. (accessed Mar. 13, 2013).
ARES product guide, 22 pages (undated).
Itamar WatchPat Flyer, 2 pages (undated).
NovaSom Accusom Home Sleep Test web page, copyright 2012, http://www.novasom.com/accusom-at-home.htm, 2 pages (accessed Mar. 13, 2013).
Partial International Search from International Application No. PCT/US2013/068962 mailed Feb. 25, 2014.
International Search Report and Written Opinion from International Application No. PCT/US2013/068962 mailed Jun. 5, 2014.
Written Opinion of the International Preliminary Examining Authority for International Application No. PCT/US2013/068962 mailed Feb. 6, 2015.
Notification of Transmittal of the International Preliminary Report on Patentability for International Application No. PCT/US2013/068962 mailed Mar. 5, 2015.

* cited by examiner

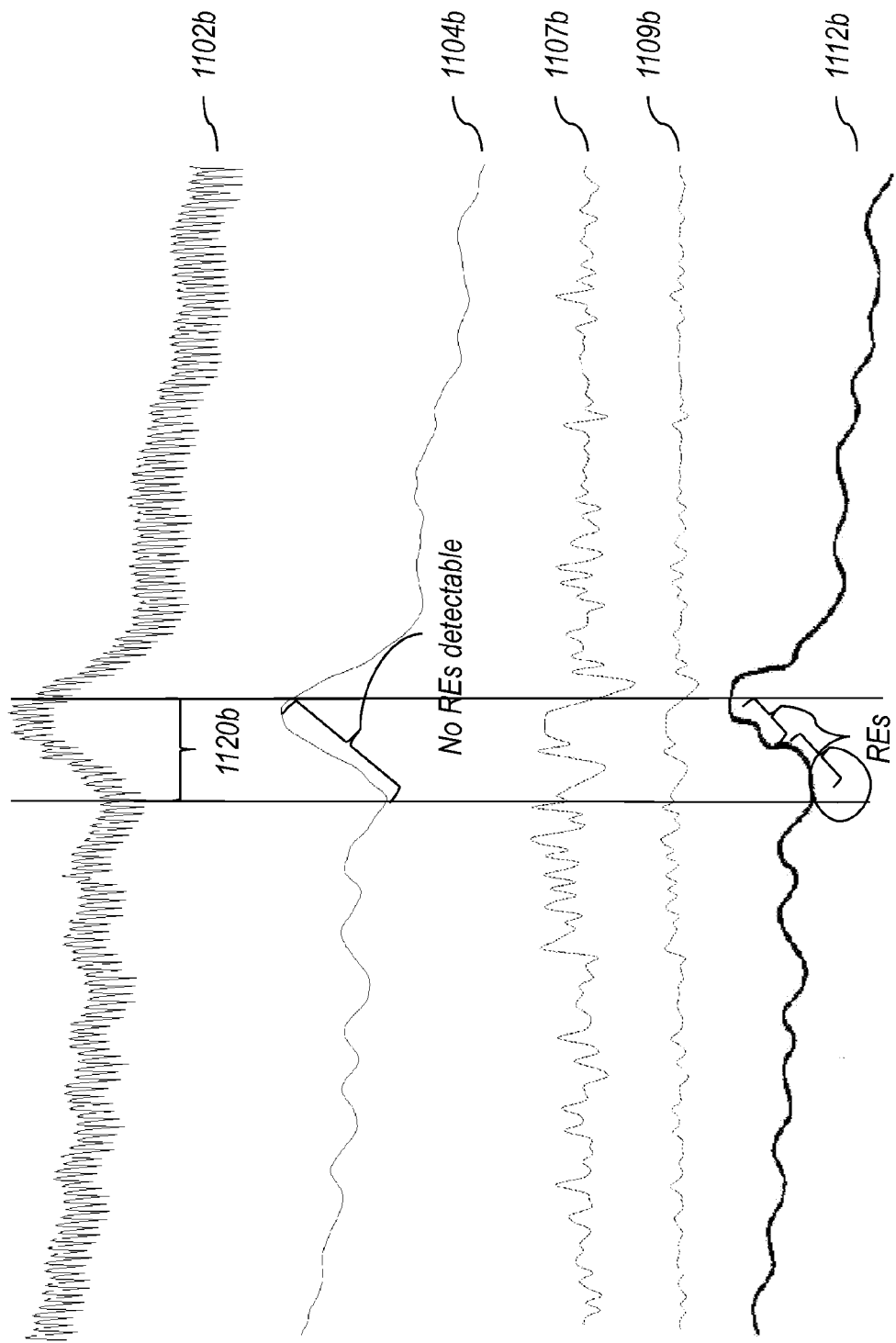

METHODS FOR DETECTION OF RESPIRATORY EFFORT AND SLEEP APNEA MONITORING DEVICES

RELATED APPLICATION

This application is a divisional application of U.S. nonprovisional application Ser. No. 13/830,736, which claims benefit of, and priority under 35 USC §119(e) from U.S. provisional application No. 61/723,682, which are incorporated by reference herein in their entirety.

FIELD

This invention relates generally to the acquisition of physiological data for health signs monitoring; and, more particularly, for the diagnosis of sleep disorders such as sleep apnea.

BACKGROUND

Obstructive sleep apnea (OSA) is the most common sleep disorder and is responsible for more mortality and morbidity than any other sleep disorder. OSA is characterized by recurrent failures to breathe adequately during sleep (termed apneas or hypopneas) as a result of obstructions in the upper airway.

Apnea is defined as a complete cessation of airflow. Hypopnea is defined as a reduction in airflow disproportionate to the amount of respiratory effort expended and insufficient to meet the individual's metabolic needs. During an apnea or hypopnea, commonly referred to as an abnormal respiratory event, oxygen levels in the brain decrease, while the carbon dioxide levels rise, causing the sleeper to awaken. During an apneic event, adrenaline and cortisol are released into blood and the heart rate and blood pressure increase. The brief arousals to breathe are followed by a return to sleep.

OSA is a serious yet treatable health problem worldwide. Published reports indicate that untreated OSA patients are three to five times more likely to be involved in industrial and motor vehicle accidents and have impaired vigilance and memory. Untreated OSA leads to hypertension, stroke, heart failure, irregular heartbeat, heart attack, diabetes and depression. Current estimates reveal that over 80% of individuals with moderate to severe OSA remain undiagnosed.

The current standard for the diagnosis of OSA is an expensive overnight sleep study—polysomnography (PSG), which is administered and analyzed by a trained technician and is reviewed by physician specializing in sleep disorders. A typical overnight PSG includes recording of the following signals: electroencephalogram, electromyogram, electrooculogram, respiratory airflow (with oronasal flow monitors), respiratory effort, oxygen saturation (oximetry), electrocardiography, snoring sounds, and body position. These signals offer a relatively complete collection of parameters from which respiratory events may be identified and OSA may be reliably diagnosed.

Obstructive apnea and hypopnea are defined as absence and reduction, respectively, in airflow, in spite of continued effort to breathe, due to obstruction in the upper airway. Typical polysomnography includes some recording of respiratory effort. The most accurate measure of effort is a change in pleural pressure as reflected by an esophageal pressure monitor. Since the esophageal pressure monitoring method is difficult to administer and highly uncomfortable to patients, other methods have been developed. These methods estimate respiratory effort and depend on measures of rib cage and abdominal motion and include inductance or impedance plethysmography, or simple strain gages.

The expense, inconvenience and complexity of traditional PSG sleep studies have created a significant need for simplified and cheaper OSA diagnostics. As a result, several portable sleep monitors have been developed over the past several years. These monitors measure fewer parameters than PSG, yet some of them offer the accuracy comparable to that of PSG. Furthermore, portable OSA monitors bring the convenience of in-home testing and are often shipped to patients after being prescribed by physician. While significantly less complex than sleep lab PSG equipment, most in-home OSA diagnostic systems require the patient to apply sensors, plug in wires, apply and adjust transducers, straps, gages and other measuring devices, or to operate a computer-controlled bedside unit. This equipment can be difficult for a lay person to apply and properly operate. One of the existing home diagnostic systems Watch-PAT, manufactured by Itamar Medical Ltd., requires patients to watch an hour-long training presentation prior to using its product. Another example of a difficult to use diagnostic system is AccuSom manufactured by NovaSom. The difficulty that patients experience in setting up in-home devices limits compliance, results in poor quality of sleep data and limits the adoption of the in-home sleep monitors. Furthermore, the equipment can be uncomfortable and the quality of the sensed data can be poor due to motion artifacts or sensors getting displaced during sleep. One of the main reasons for poor quality of sleep data is the currently available respiratory effort sensors. Respiratory effort sensors are typically designed as chest or abdominal bands measuring chest expansion and are based on inductive plethysmography, piezo-electric crystals, conductive elastomers, magnetometers and strain gauges. These respiratory effort sensors are particularly prone to motion artifacts and trapping. Occurrence of trapping artifacts, as a patient turns from one side to another, may significantly affect the quality of respiratory effort data. Two studies found the failure rate for effort bands ranged between 7% and 21% even when the bands are applied by a trained sleep study technician.

Thus, a device that eliminates or reduces the use of wires, and can be reliably self-applied with minimal instruction would be beneficial to accurately diagnose patients at risk for OSA. Furthermore, a device that can detect respiratory effort without the use of an effort band would offer the convenience and improve the quality of sensed respiratory effort data by eliminating trapping artifacts.

There is a known device—ARES—manufactured by Watermark Medical Inc., which detects respiratory effort by assessing "forehead venous pressure" and is based on an algorithm combining signals from a photoplethysmography sensor, a pressure sensor and an accelerometer. The device includes nasal tubes for the assessment of nasal airflow and a bulky main unit that is attached to the patient's forehead with straps. Due to its form factor and size, the use of airflow tubes and the types of sensors used, the device is uncomfortable to sleep in, and may be prone to sensor displacement and poor quality of sleep data.

There is also a known device—SleepStrip, which incorporates three thermistors to measure oronasal airflow, a battery, a microcontroller and a memory in a strip which is applied with adhesive to patient's face. However, due to the lack of the sensors for oxygen saturation or respiratory effort, this device is only suitable for screening patients for abnormal airflow and is not sufficient for the detection of OSA. While abnormal airflow is a key symptom of OSA, the respiratory effort during apnea and hypopnea is the physiologic parameter that distinguishes OSA from other forms of sleep-disordered breathing such as central sleep apnea.

One method proposes the use of photoplethysmography for the detection of respiratory effort without the use of effort belts. When analyzing the photoplethysmography (PPG) signal during an apneic event, it has been suggested to use a low-pass filter or a frequency analysis to identify respiratory induced intensity variation (U.S. Pat. No. 7,690,378). However, these intensity variations are not exclusively due to respiratory effort and therefore, an application of a low-pass filter or a frequency analysis is insufficient to identify respiratory effort during apneic events. There are several possibilities as to the origin of these intensity variations. Inspiration results in a momentary reduction in stroke volume and, therefore, a corresponding reduction in cardiac output, which has an effect on the pulsatile component of the PPG waveform. Also there are blood volume changes during the respiratory cycle due to the transmitted changes in intra-thoracic pressure. Additionally, it has been shown that sympathetically mediated vasoconstriction of the arteries also plays a part in PPG intensity variations. It is desired to have a method and system that eliminates the role of sympathetically mediated vasoconstriction from PPG intensity variations during apneic events in order to accurately identify respiratory effort.

An easy-to-apply and easy-to-operate diagnostic device, which incorporates the sensors for accurate detection of respiratory events and respiratory effort, is still needed for convenient in-home sleep apnea diagnosis.

SUMMARY

In a general aspect, the present invention relates to a device for diagnosis of sleep apnea. The device includes a waterproof housing within which sensors for airflow, oxygen saturation, heart rate, and respiratory effort analysis are contained. The housing also includes a battery, a microprocessor, and either an onboard memory to store the data from the sensors or a wireless data transmission system. The housing may contain an adhesive surface to be affixed to patient's skin.

In one embodiment, the device includes a housing shaped to fit the contours of the patient's face, at least one pair of photosensors positioned to detect blood volume in the face of the patient, and at least one air-flow sensor positioned to detect airflow during breathing of the patient. The device further includes a memory disposed in the housing and configured to store physiological information related to the detected blood volume and store physiological information related to detected airflow during breathing. The device further includes a controller disposed in the housing and configured to control at least one pair of photosensors, to detect blood volume, to control at least one airflow sensor to detect airflow, and the memory to store physiological information related to the detected blood volume and store physiological information related to the detected airflow during breathing, during a predefined monitoring period.

In some embodiments, the device and methods analyze a plethysmography signal (e.g., photoplethysmography) for a slow-moving component ("DC component") corresponding to changes in blood volume and a fast-moving component ("AC component") corresponding to arterial pulse waves. The DC component may be used as an estimate of a PPG intensity variation.

In another general aspect, the present invention relates to a computer program product comprising of a computer useable medium having computer readable program code functions embedded in said medium for causing a computer to acquire and analyze physiological signals reflective of respiratory effort.

Implementations of the device may include one or more of the following. The airflow data may be collected with different types of sensors: thermistors or gas flow sensors, for instance. The blood oxygen saturation may be detected with two pairs of photo-emitters and receptors. The heart rate data may be obtained from the photoplethysmography (PPG) signal. The patient's position and movement may be obtained with an accelerometer. The device may include a microcontroller, a power source and an onboard memory to store collected data, or a wireless data transmission system to send the collected data.

Implementations of the method may include one or more of the following. Data on respiratory effort can be obtained indirectly by analyzing changes in intra-thoracic pressure as evidenced by the changes in the volume of blood vessels. The trends in the blood volume may be estimated from the PPG signal obtained from peripheral vessels, such as nasal blood vessels.

In one embodiment, a method detects respiratory effort during a respiratory event. The method comprises obtaining oxygen saturation, heart rate and airflow data, analyzing the data to identify a respiratory event, and analyzing the peripheral plethysmography data to identify respiratory effort during the respiratory event. The respiratory effort may be identified by detecting changes in the DC component of the plethysmography data during an onset of the respiratory event, estimating effect of autonomous nervous system on the DC component of the plethysmography data during the respiratory event, and subtracting the effect of the autonomous nervous system from the plethysmography data to obtain the respiratory effort.

The described devices and methods provide reliable and accurate detection of apneic and hypopneic respiratory events. The described devices and methods are also simpler, more convenient to use and less expensive than other known techniques.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 2b is a block diagram illustrating one embodiment and the main components of the diagnostic system of FIG. 2a.

FIGS. 11a and 11b are timing diagrams illustrating the analytical steps of one embodiment of an operation of the diagnostic system for identifying respiratory effort in first and second examples of PPG signals.

DETAILED DESCRIPTION

Various embodiments of the present invention are now described with reference to the figures where like reference numbers indicate identical or functionally similar elements. Also in the figures, the left most digits of each reference number corresponds to the figure in which the reference number is first used.

Reference in the specification to "one embodiment", "an embodiment", "various embodiments" or "some embodiments" means that a particular feature, structure, or characteristic described in connection with these embodiments is included in at least one embodiment of the invention, and such references in various places in the specification are not necessarily all referring to the same embodiment.

All publications, patents, and patent applications cited herein are hereby incorporated by reference in their entirety for all purposes to the same extent as if each individual publication, patent, or patent application were specifically and individually indicated to be so incorporated by reference.

Methods and apparatus diagnose irregular or abnormal respiratory activity of a patient. In various illustrative embodiments, such methods and apparatus are described below for obstructive sleep apnea, but such methods and apparatus may be used in other applications. For example, the methods and apparatus may be used to monitor respiratory activity of a patient recovering from the effects of anesthesia after surgery in which the patient is becoming able to breathe on his own without the assistance of a ventilator as the anesthesia wears off. As another example, the methods and apparatus may be used in critical care units, intensive care units, trauma centers, or emergency rooms to monitor, analyze, and diagnose respiratory activity of patients who, for example, have received head or other bodily trauma, or have overdosed on drugs. As yet another example, the methods and apparatus may be used in medical facilities in which the patient has local anesthesia for outpatient surgery.

A sleep apnea diagnostic system includes a housing that is configured to be attached to near the nose of a patient's face to sense physiological information of a patient. The housing includes sensors to sense the physiological information. The physiological information may be, for example, air flow through the nose or the mouth or both. The physiological information further may be, for example, blood oxygenation. The sleep apnea diagnostic system includes at least one processor in the housing or external to the housing or both to analyze the physiological information to determine whether the patient has experienced irregular or abnormal respiratory activity. The analysis may be real time or delayed.

Figure 1:
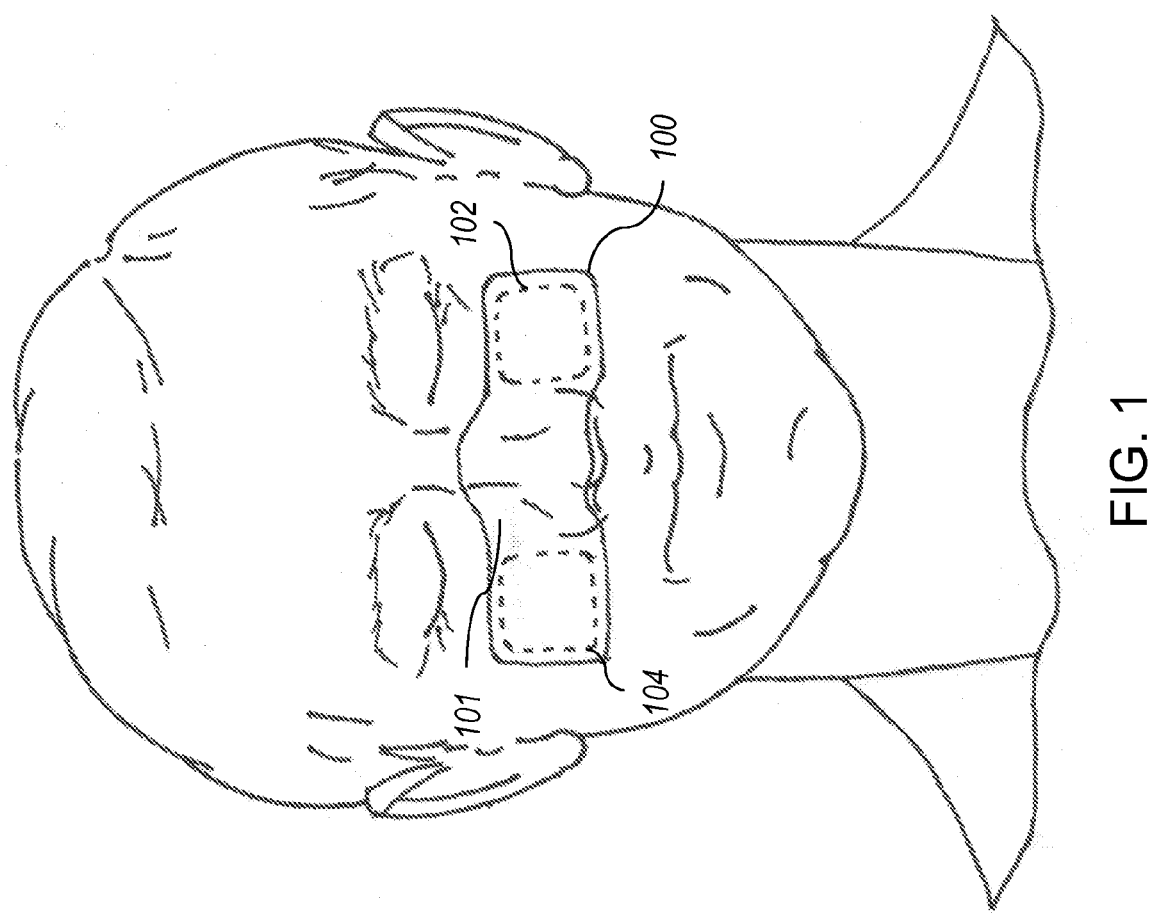
FIG. 1 is a schematic diagram illustrating placement of the sleep apnea diagnostic system in accordance with the present invention.

Referring to FIG. 1, an exemplified sleep apnea diagnostic system 100 is contained inside a flexible housing 101, which is adapted to fit the contours of the patient's face. The housing 101 includes adhesive surfaces 102 and 104 disposed on left and right sides, respectively, of a back surface of the housing 100 that can be affixed to the patient's skin. The use of the terms "front", "back", "left" and "right" are for convenience and are not to be construed as limiting. In some embodiments, the housing 101 may be affixed to the patient using straps (not shown). The adhesive surfaces 102 and 104 may be selected to provide sufficient adhesion to the patient under typical sleep conditions for at least a monitoring period (e.g., four hours). In some embodiments, the housing 101 is made of a flexible bio-compatible polymer to enhance patient's comfort. In some embodiments, the housing 101 is water resistant. In various embodiments, the housing 101 is shaped to fit the skin surface of the patient's nose, upper lip and the area of maxillary sinuses.

Figure 2A:
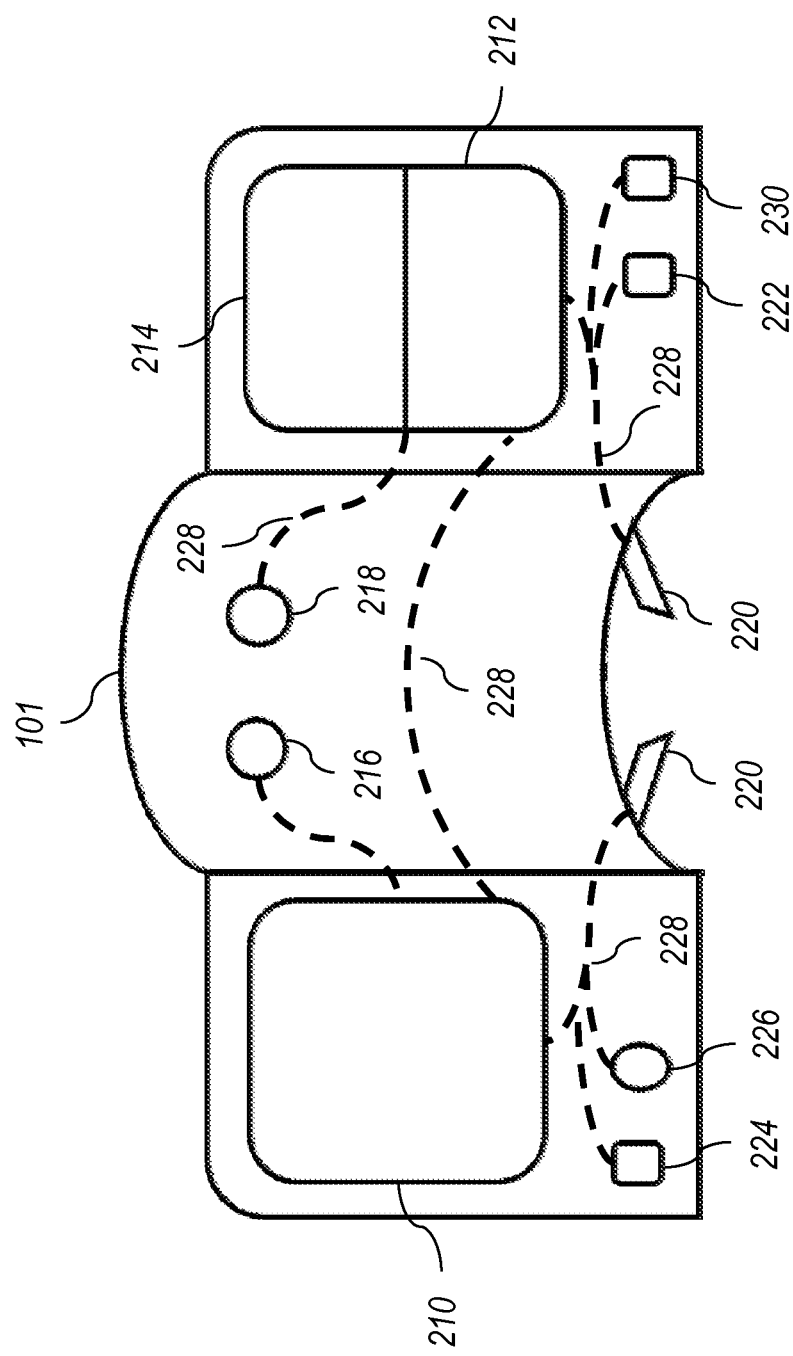
FIG. 2a is a schematic diagram illustrating one embodiment and the main components of the diagnostic system of FIG. 1 for the detection of sleep apnea.
Figure 2B:
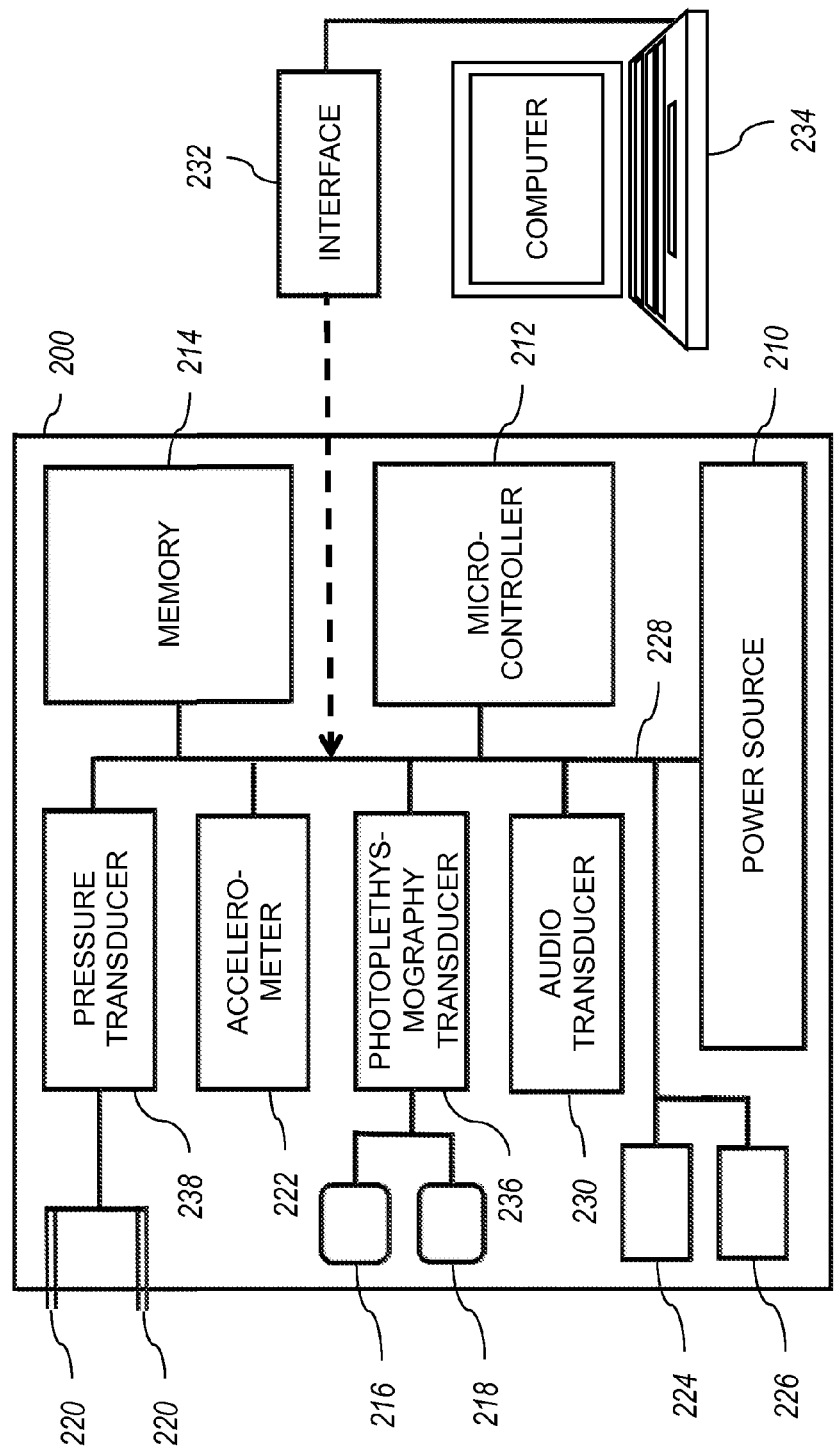

Referring to FIGS. 2a and 2b, the diagnostic system 100 includes the housing 101, comprising the following electronic components. A battery 210 may be made of a lithium-polymer or any other material with enough capacity to provide power to other electronic components within the housing 101 for at the monitoring period. A microcontroller 212 operates other electronic components and stores the sensed physiological data in a memory 214. The microcontroller 212 may be, for example, a controller, a microprocessor or a processor. The memory 214 is sized to store the physiological data recorded for at least the monitoring period. The memory 214 may also store program code for the microcontroller 212. Two photo-emitters 216 and a photo-sensor 218 are positioned on the opposite sides of the patient's nose to collect heart or pulse rate, blood oxygen saturation data, and photoplethysmography data. In some embodiments, the photo-emitters 216 and the photo-sensor 218 emit and measure reflection or absorption of light wavelengths typically reflected or absorbed by oxygenated and desoxygenated hemoglobin. Although two photo-emitters 216 and a photo-sensor 218 are described, other numbers of photo-emitters 216 and photo-sensors 218 may be used. The photo-emitters 216 and the photo-sensor 218 are coupled to a photoplethysmography transducer 236. The photoplethysmography transducer 236 processes and converts the sensed physiological data from the photo-sensor 218 into a suitable data format for the microcontroller 212 and the memory 214. The photoplethysmography transducer 236 processes and converts control signals from the microcontroller 212 into appropriate signals for the photo-emitters 216. Two air-flow sensors 220 protrude from the housing 101 and are positioned (e.g., near or inside the nostrils of the patient) to measure nasal airflow. An optional third air-flow sensor (not shown) may be attached to the housing 101 in a similar fashion and positioned over the patient's mouth to measure oral airflow. In some embodiments, the air-flow sensors 220 are air-pressure sensors or temperature sensors or a combination of both. The air-flow sensors 220 are coupled to an air-flow transducer 238 that processes and converts the sensed physiological data from the air-flow sensors 220 into a suitable data format for the microcontroller 212 and the memory 214. The air-flow sensors 220 may be mounted to a distal end of tubing that is disposed to extend from the housing 101. The tubing may be detachable from the housing 101. In some embodiments, the air-flow transducer 238 is an air pressure transducer.

An accelerometer 222 may be included to detect position and motion of the patient as an indication of sleep state. A switch 224 may be included to allow the patient or a health care worker to initiate and to terminate the sleep data collection. An electrical indicator 226 may be incorporated into the housing 101 to indicate when the system 100 is collecting data. Interconnection 228 runs completely inside the housing 101 and connects the sensors 216, 218, and 220 with other electronic components. In some embodiments, interconnection 228 is a bus. In various embodiments, interconnection 228 is wiring. The sensors 216, 218, and 220 and the accelerometer 222 may send sensed signals to the microcontroller 212. The sensed signals may be in analog or digital form. In some embodiments, the sensors 216, 218 are physically removable from the housing 101 and electrically detachable from the photoplethysmography transducer 236 to thereby be replaceable. In some embodiments, the sensors 220 are physically removable from the housing 101 and electrically detachable from the air-flow transducer 238 to thereby be replaceable. The microcontroller 212 may include an analog-to-digital (A/D) converter for digitizing the sensed signals. An audio transducer 230 may monitor the patient to detect snoring or other respiratory activity. An internal timer (not shown) is used by the microcontroller 212 to generate time stamps or time differences or for controlling operations.

A computer 234 is coupled via an interface 232 to the interconnection 228. In some embodiments, the diagnostic system 100 is placed on a patient to sense physiological information. The diagnostic system 100 is then later coupled to the computer 234 to download the sensed physiological information from the memory 214 to the computer 234. The interface 232 may include a physical connection to the diagnostic system 100 or may be wireless to a wireless system (not shown) in the housing 101. The computer 234 performs the data analysis described in conjunction with FIGS. 3-11. In some embodiments, the data analysis described in conjunction with FIGS. 3-11 is performed by the microcontroller 212 or a combination of the microcontroller 212 and the computer 234.

Although the analysis of FIGS. 3-11 is described for a PPG signal, other signals, such as impedance, volume plethysmography, and tissue plethysmography, may be used.

Figure 3:
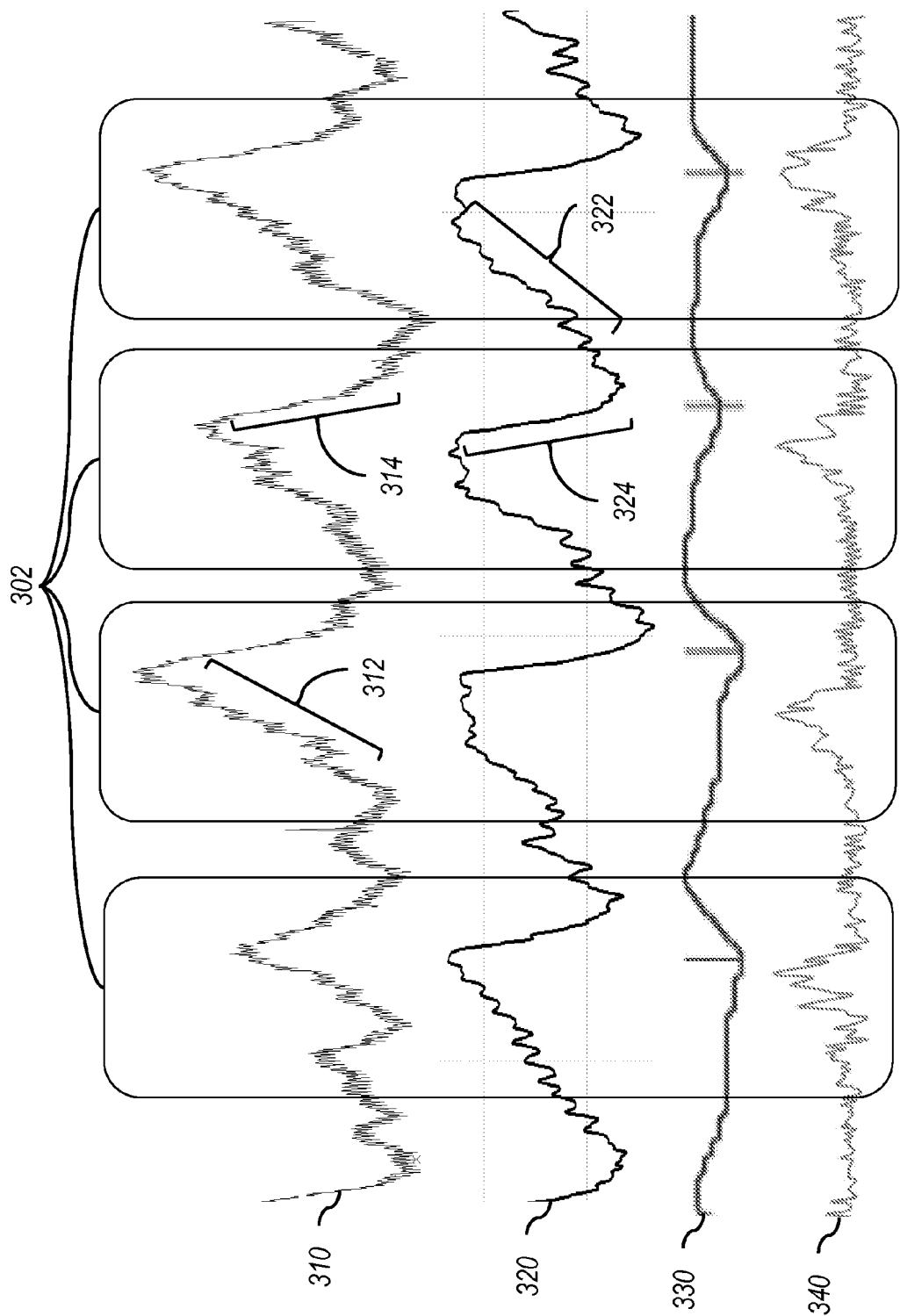
FIG. 3 is a timing diagram illustrating measured signals with one embodiment of the diagnostic system.

Referring to FIG. 3, the timing diagram shows collected signal data and computed data for the detection of respiratory events. Graph 310 is a photoplethysmography signal consisting of the fast moving component ("AC component") reflective of pulse waves sent through the arteries by contracting heart muscle and the slow moving component ("DC component") reflective of slower changes in tissue blood volume. Graph 320 is a signal recorded from the thermistors (air-flow sensors 220) and reflective of changes in airflow. Graph 330 represents calculated data on oxygen saturation. Graph 340 shows changes in heart rate and is calculated from the photoplethysmography data. The data in graphs 310 and 320 was collected simultaneously and shows four respiratory events 302. An onset of a respiratory event is characterized by reduction or absence of tidal airflow and gradual increase in the temperature sensed by the thermistor (for instance, 322), a gradual increase in the DC component of the photoplethysmography signal (for instance, 312), a decrease in oxygen saturation and an increase in heart rate. The termination of a respiratory event is characterized by return to breathing, typically with a first large breath, which is reflected by a decrease in the temperature signal sensed by the thermistor (for instance, 324) and an increase in light absorption as reflected in the DC component of the photoplethysmography signal (for instance, 314). After the respiratory event is terminated, oxygen saturation recovers and heart rate returns to baseline. Therefore, by monitoring and analyzing the patterns in the three parameters (airflow data, oxygen saturation level and the calculated heart rate), respiratory events may be identified. An apneic episode or event can be distinguished from a hypopneic episode by the degree of reduction in airflow. An absence of tidal airflow would indicate an apneic event and a significant reduction in the amplitude of tidal airflow would indicate a hypopneic event.

Figure 4:
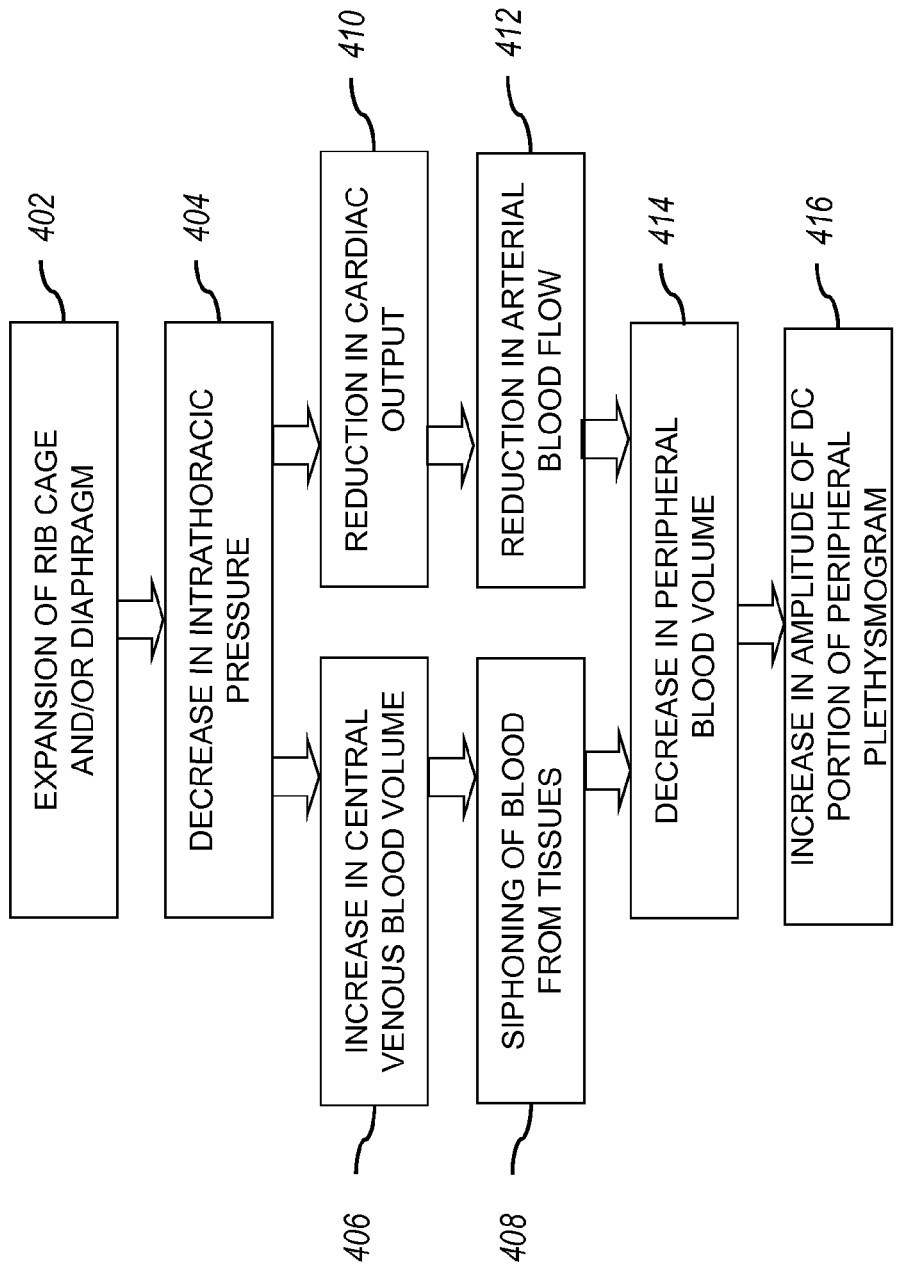
FIG. 4 is a flow chart illustrating effect of an apneic respiratory effort on peripheral blood volume.

Referring to FIG. 4, the flow chart illustrates some of the main physiological changes that occur during an apneic respiratory event and the effect of these changes on certain parameters of peripheral photoplethysmogram. When a person breathes, the pressure inside the chest cavity, called the intra-thoracic pressure, changes with each breath. As a person inhales, the chest expands resulting in a decrease in intra-thoracic pressure, which draws air into the lungs. During an exhalation, the intra-thoracic pressure increases and forces air out of the lungs. These changes in intra-thoracic pressure also cause changes in the amount of blood returned to the heart via veins and the amount of blood pumped by the heart into arteries. During an obstructive apneic respiratory event, the airflow into the lungs is blocked, and an expansion of rib cage and diaphragm (402) results in a decrease in intra-thoracic pressure (404), which remains lowered due to the lack of air inflow. The low intra-thoracic pressure causes the central veins located in the chest cavity to expand causing an increase in blood volume inside the veins. This leads to an overall increase in central venous blood volume (406), and a siphoning of venous blood from tissues (408). This also leads to a reduction in cardiac output (410), and a reduction in arterial blood flow (412). As a result, the amount of blood in peripheral blood vessels is temporarily decreased (414). This effect on the peripheral blood volume can be estimated by detecting a temporary increase in the slow moving (DC) component of peripheral photoplethysmogram (416).

These changes in the DC component of peripheral photoplethysmogram can be reliably assessed only when the photoplethysmography sensor (e.g., sensors 216 and 218) is positioned over a highly vascularized area from which the venous blood drains into a large vein located closely to vein cava. There are only a few places on the human body where this criterion can be met. Nasal positioning of a photoplethysmography sensor (e.g., sensors 216 and 218) is one such location where measurements of airflow and respiratory effort, by the method described in this embodiment of the disclosure, can be combined into a single unit device without the use of long tubes or wires. While most of the known sleep apnea diagnostic devices rely on a photoplethysmography signal from a distal location, such approaches result in the PPG signal being dominated by the effects of the sympathetic nervous system. Therefore, such approaches cannot reliably assess changes in peripheral blood volume as a measure of respiratory effort during an apneic episode. Nasal positioning of the PPG sensors (e.g., sensors 216 and 218) results in a signal which is influenced by both the respiratory effort and the effects of the sympathetic nervous system. Such positioning makes it feasible to distinguish the respiratory effort from the effects of the sympathetic nervous system.

Figure 5:
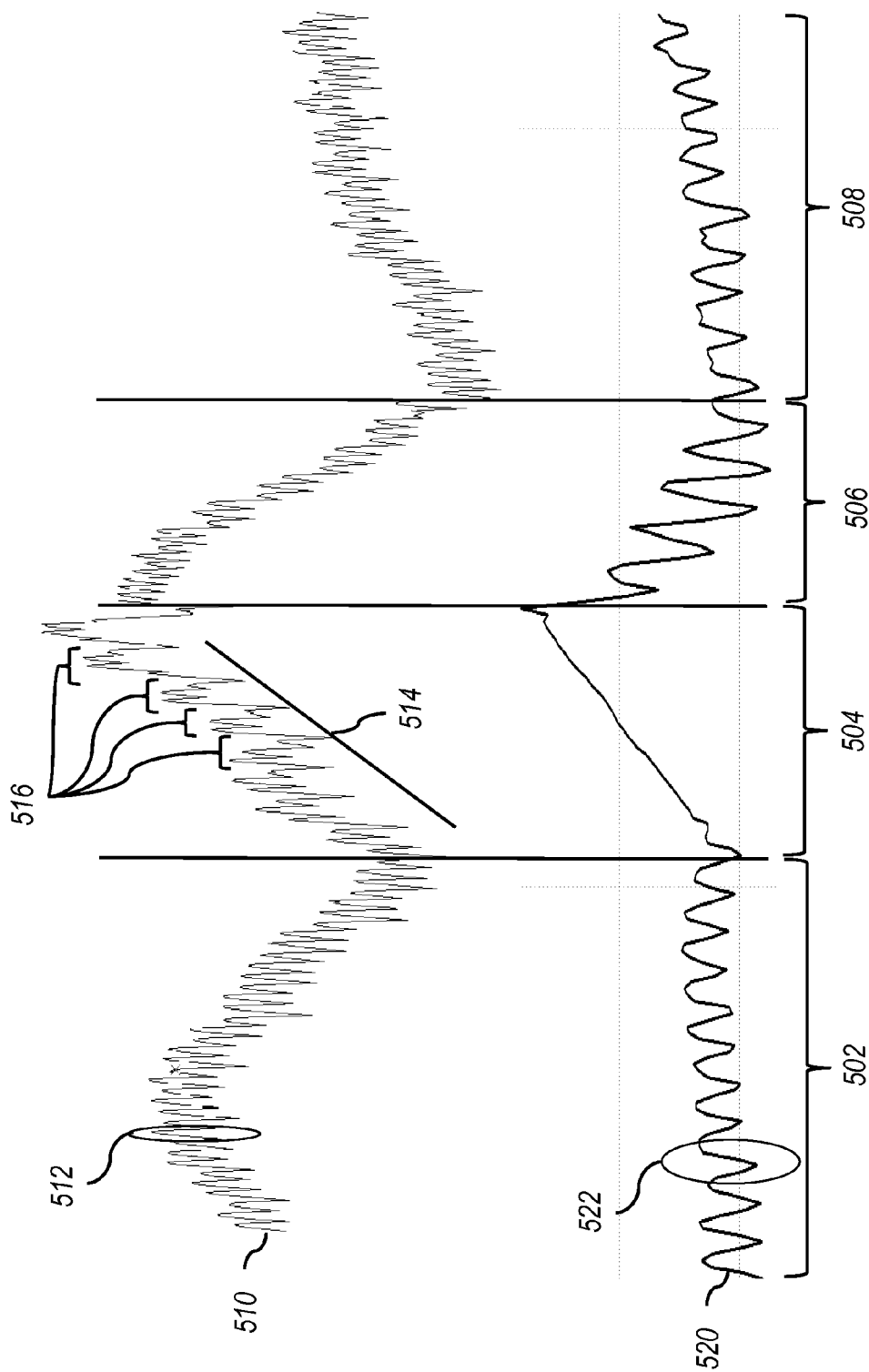
FIG. 5 is a timing diagram illustrating features of measured signals during an apneic episode with respiratory effort.

Referring to FIG. 5, the timing diagram shows an example of photoplethysmography signal 510 and airflow signal 520 collected during a time period in which an obstructive apneic event 504 occurred. Airflow data in graph 520 was collected with a thermistor (air-flow sensor 220) and shows a pre-apneic normal breathing during a time period 502. Each reduction and a subsequent increase in measured temperature 522 correspond to one breath. The onset of the apneic event 504 is characterized by a complete cessation of breathing as evidenced by the absence of tidal airflow. The data shows a post-apneic recovery 506 characterized by changes in temperature induced by tidal airflow. A time period 508 shows normal breathing.

Photoplethysmography signal 510 was collected simultaneously with the airflow data and shows a slow-moving (DC) component corresponding to changes in blood volume and a fast-moving (AC) component corresponding to arterial pulse waves 512. During the onset of the apneic event 504, the DC component gradually increases. During this increase 514, the DC component changes with the frequency similar to the breathing rate of the patient. These fluctuations in the DC component are reflective of respiratory effort that takes place during the complete cessation of breathing. Each respiratory effort 516 alters the DC level such that the minimums of the pulsatile AC component are not aligned with the line 514 approximating the overall increase in the DC level.

Figure 6:
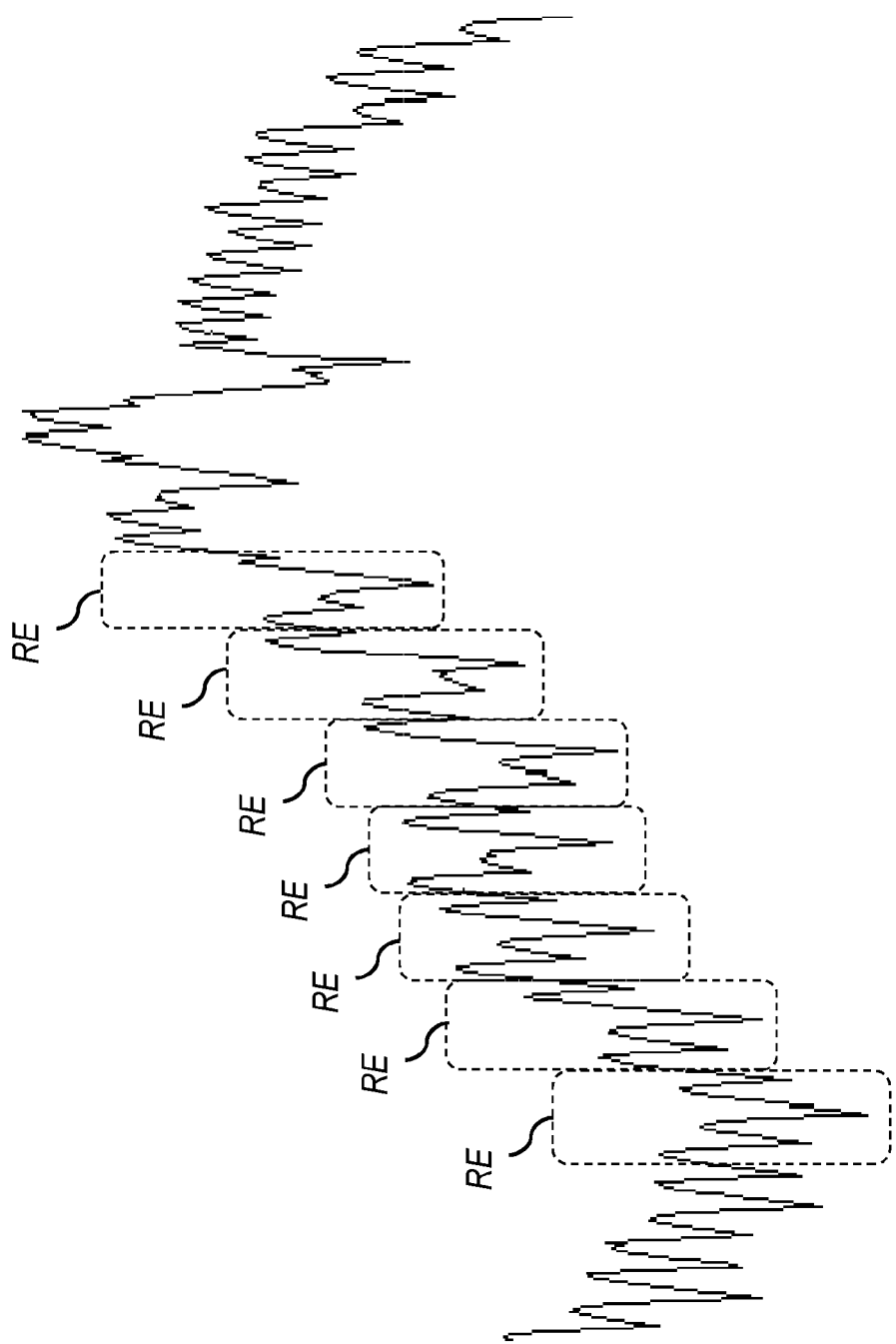
FIG. 6 is a timing diagram illustrating features of a photoplethysmography signal during an onset of apneic episode with respiratory effort.

Referring to FIG. 6, the timing diagram provides an expanded view of the photoplethysmography signal 510 collected during an onset of the apneic event 504 described in FIG. 5. In this specific example, each respiratory event RE consists of three pulse waves whose minimums follow the same pattern. As the patient expands his rib cage in an attempt to draw air into his lungs, the decrease in DC level (or the minimums of the pulse waves) is followed by an increase corresponding to the end of the respiratory effort.

Figure 7:
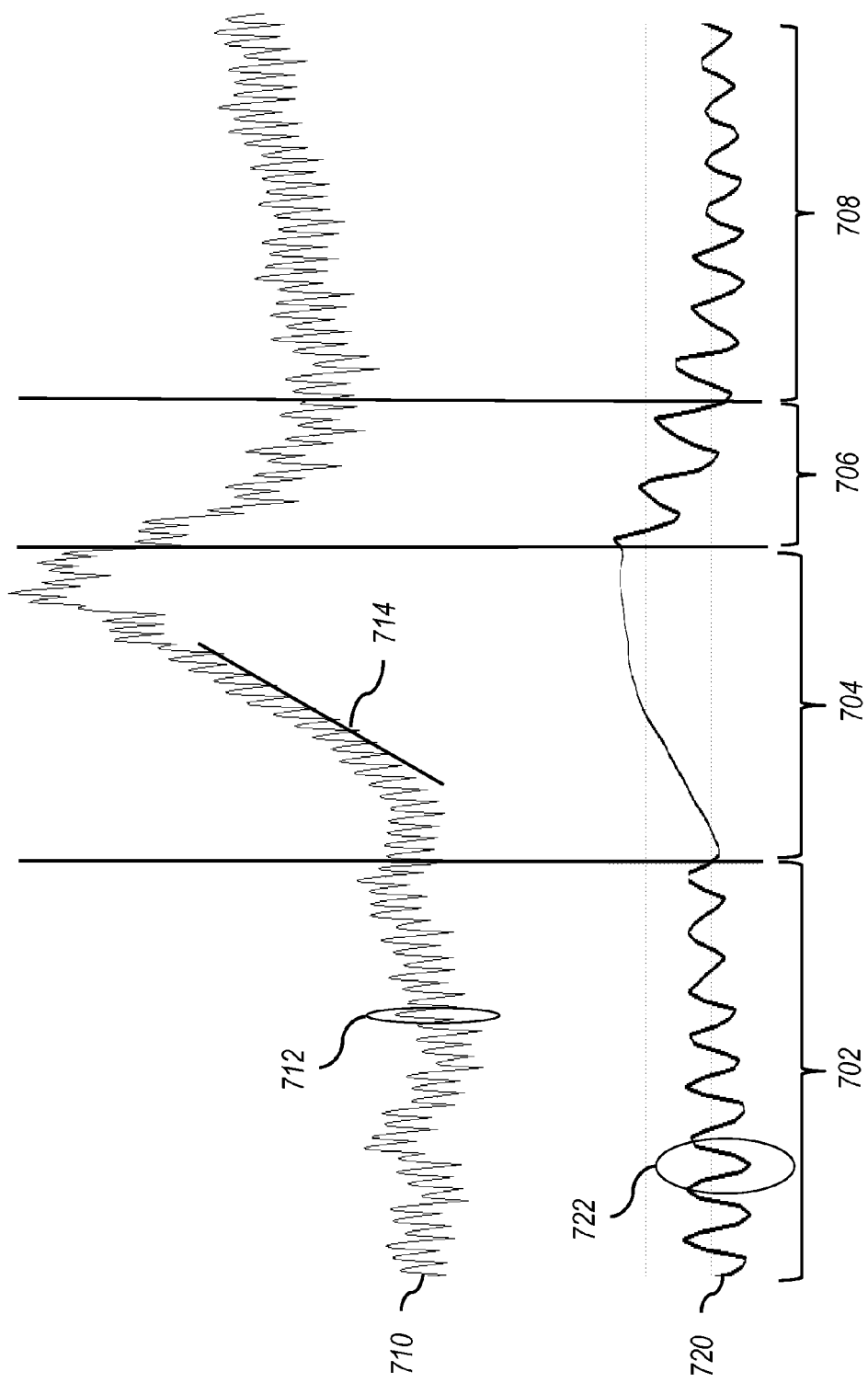
FIG. 7 is a timing diagram illustrating features of measured signals during an apneic episode without respiratory effort.

Referring to FIG. 7, the timing diagram shows an example of photoplethysmography signal 710 and airflow signal 720 collected during a time period in which a central apneic 704 event occurred. Airflow data in graph 720 was collected with a thermistor (air-flow sensor 220) and shows pre-apneic normal breathing during a time period 702. Each reduction and a subsequent increase 722 in measured temperature correspond to one breath. The onset of the apneic event 704 is characterized by a complete cessation of breathing as evidenced by the absence of tidal airflow. The data shows a post-apneic recovery 706 characterized by tidal airflow induced changes in temperature. A time period 708 shows normal breathing.

Photoplethysmography signal 710 was collected simultaneously with the airflow data and shows a slow moving (DC) component corresponding to changes in blood volume and a fast moving (AC) component corresponding to arterial pulse waves 712. During the onset of the apneic event 704, the DC component gradually increases. During this increase 714, the DC component does not change with the frequency corresponding to the breathing rate of the patient. The absence of such fluctuations in the DC component is indicative of the lack of respiratory effort during apneic episodes in central apnea. The minimums of the pulsatile AC component are aligned with line 714 approximating the overall increase in the DC level.

FIGS. 5, 6 and 7 are examples of physiological data collected from patients in whom the influence of the sympathetic nervous systems on the PPG DC component is minimal. However, in most patients the effect of the sympathetic nervous system on the PPG DC component is comparable to or larger than that of respiratory effort. In such patients, the changes in the PPG DC component are a combination (or superposition) of the two effects. As related to the diagnosis of sleep apnea, if the effect of the sympathetic nervous system is significant, a patient with a central sleep apnea will exhibit changes in the PPG DC component that could be mistaken for respiratory effort and an incorrect diagnosis of obstructive sleep apnea rather than central sleep apnea could be made. Therefore, in order to correctly identify respiratory effort, the effect of the sympathetic nervous system is estimated and subtracted from the PPG DC component.

Figure 8:
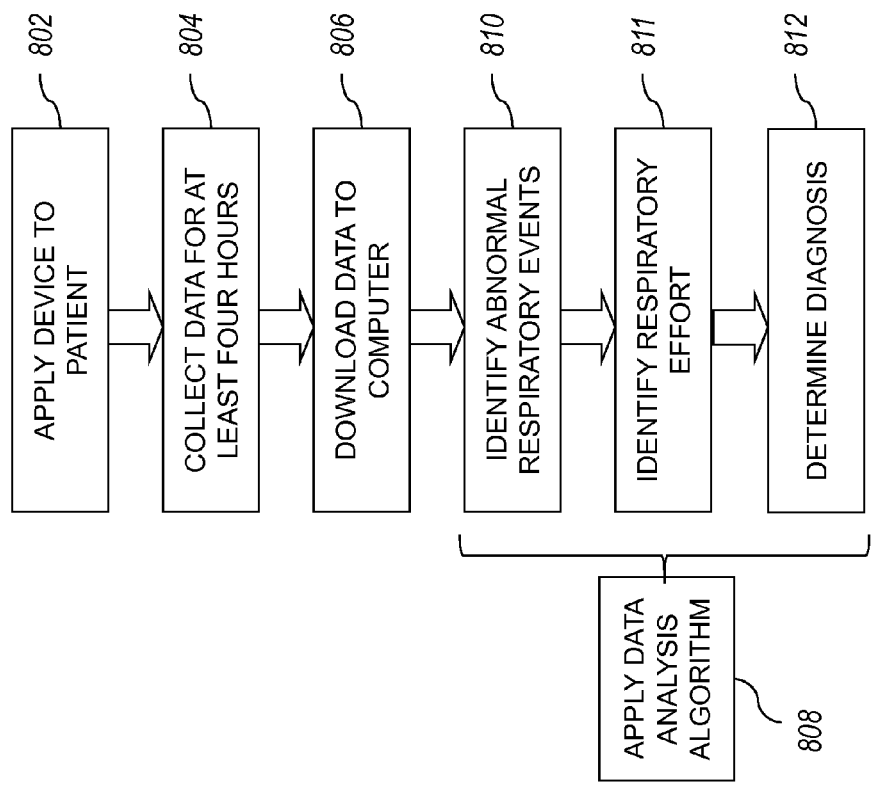
FIG. 8 is a flow chart illustrating one embodiment of an operation of the diagnostic system for the detection of sleep apnea.

Referring to FIG. 8, the flow chart illustrates the main steps in using the diagnostic system 100 and method for the diagnosis of sleep apnea. At 802, the diagnostic system 100 is applied to the patient and is secured in place. The diagnostic system 100 may be affixed with the adhesive surfaces 102 and 104 to the skin of the patient. The air-flow sensors 220 are positioned near or inside the nostrils of the patient to measure nasal airflow. The photo-emitters 216 and the photo-sensor 218 are positioned on the opposite sides of the patient's nose to collect blood oxygenation data and photoplethysmography data. Once the diagnostic system 100 is positioned, at 804, the microcontroller 212 initiates data collection and continues data collection for at least a predefined time (e.g., for at least four hours) while the patient is asleep. The data from the accelerometer 222 embedded in the air-flow transducer 238 may aid in identifying the time periods during which the patient is asleep to ensure that the battery power of the battery 210 is used only when sleep data is collected. In some embodiments, the microcontroller 212 may collect data before the patient falls asleep. The internal timer (not shown) may be used to identify the time periods during which the patient is awake or asleep. At 806, the collected sleep data may be downloaded from the memory 214 to the computer 234, after the patient returns the diagnostic system 100 for analysis or transmitted while or after the diagnostic system 100 is attached to the patient. At 808, the computer 234 applies data analysis algorithms to the collected data to compute oxygen saturation, heart rate and to identify respiratory events.

At 810, the computer 234 identifies abnormal respiratory events from the sensed physiological data. The identification may be as described above in conjunction with FIGS. 3 and 5-7 or by other known methods. Additional data analysis algorithms are used to detect respiratory effort during apneic respiratory events. These algorithms may include applying frequency filters to the photoplethysmography data to identify presence of DC waves corresponding to respiratory rate. Other approaches may include a spectral analysis (such as a Fourier analysis) or any other type of analysis, including visual inspection of the data by a technician. At 811, the computer 234 identifies respiratory efforts for the sensed physiological data, such as by the process of FIG. 9. At 812, the computer 234 determines the diagnosis of the respiratory activity, such as obstructive sleep apnea, based on the type, frequency and severity of respiratory events and the presence of respiratory effort during apneic events. Diagnosis and scoring of the respiratory events may be automatic or involve manual scoring by a trained technician or a physician.

Figure 9:
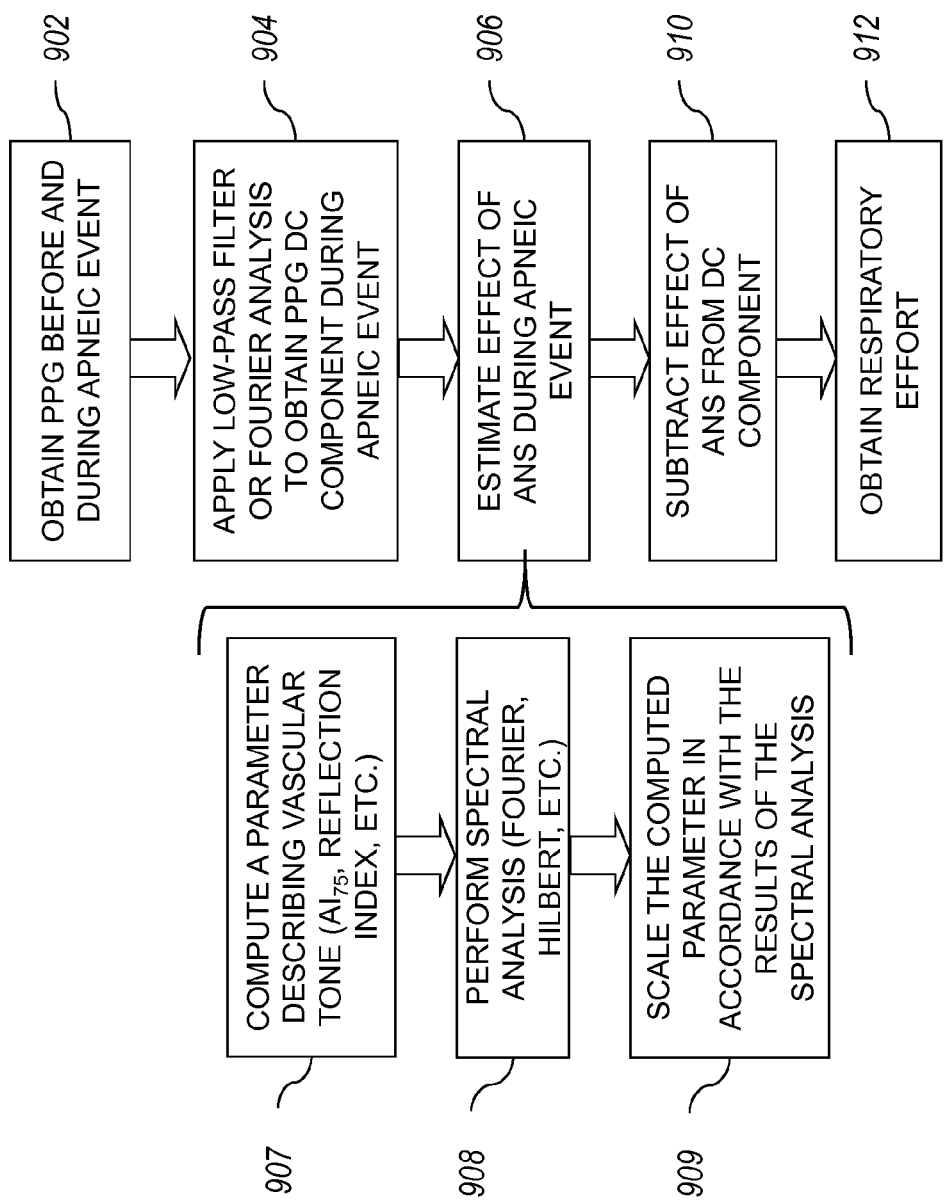
FIG. 9 is a flow chart illustrating one embodiment of an operation of the diagnostic system for identifying respiratory effort.
Figure 11A:
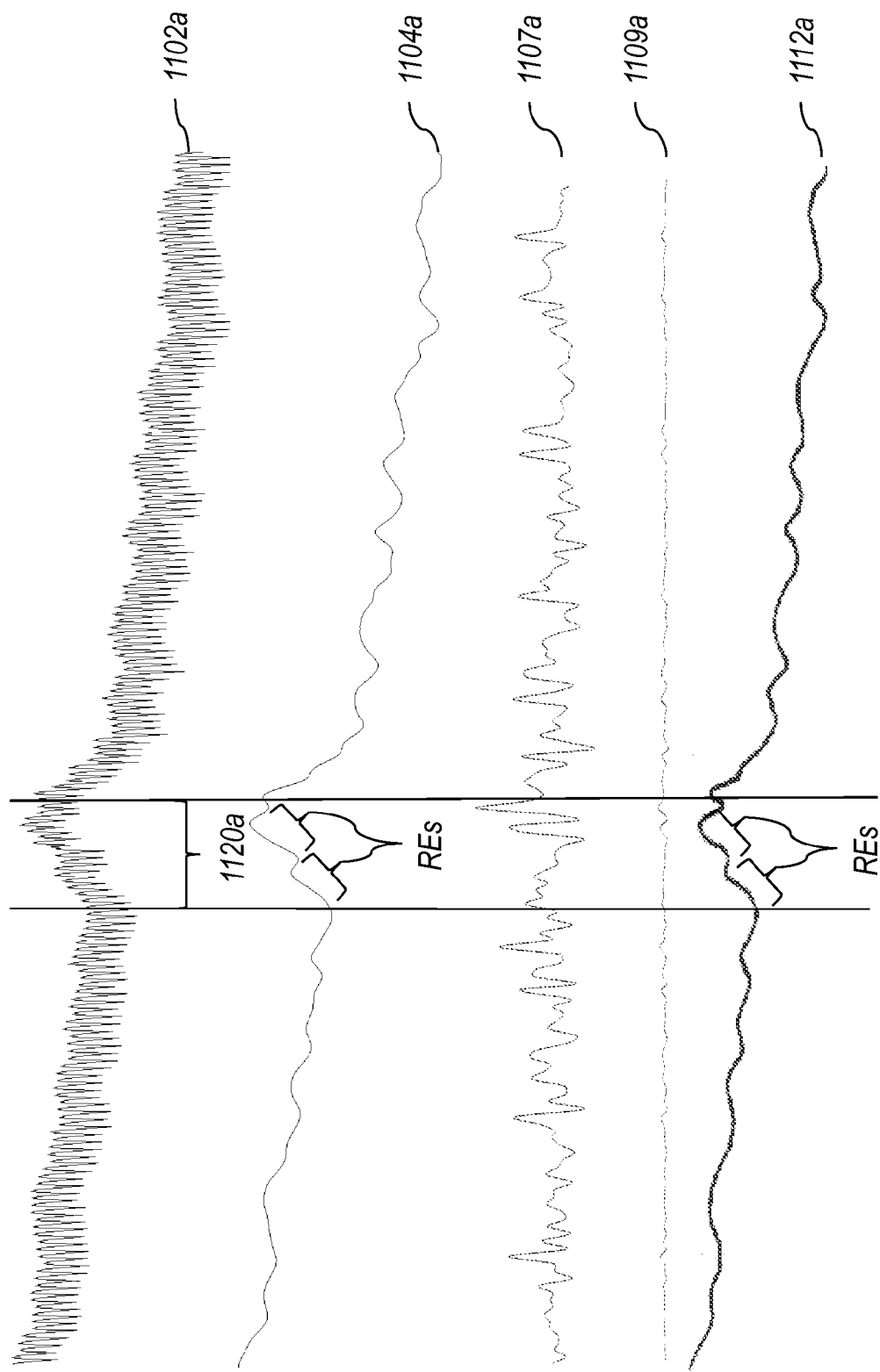

FIG. 9 is a flow chart illustrating one embodiment of an operation of the diagnostic system for identifying respiratory effort. At 902, the computer 234 obtains a PPG signal before and during an apneic event. FIGS. 11*a* and 11*b* are timing diagrams illustrating the analytical steps of one embodiment of an operation of the diagnostic system 100 for identifying respiratory effort of FIG. 9, and is described in conjunction with FIG. 9. A line 1102*a* (FIG. 11*a*) is an illustrative example of a PPG signal obtained at 902 for a signal in which respiratory events are detectable using only low passing filtering. In contrast, a line 1102*b* (FIG. 11*b*) is an illustrative example of a PPG signal obtained at 902 for a signal in which respiratory events are not detectable using only filtering. Respiratory events occur during a period 1120*a* (FIG. 11*a*) and 1120*b* (FIG. 11*b*).

Figure 10:
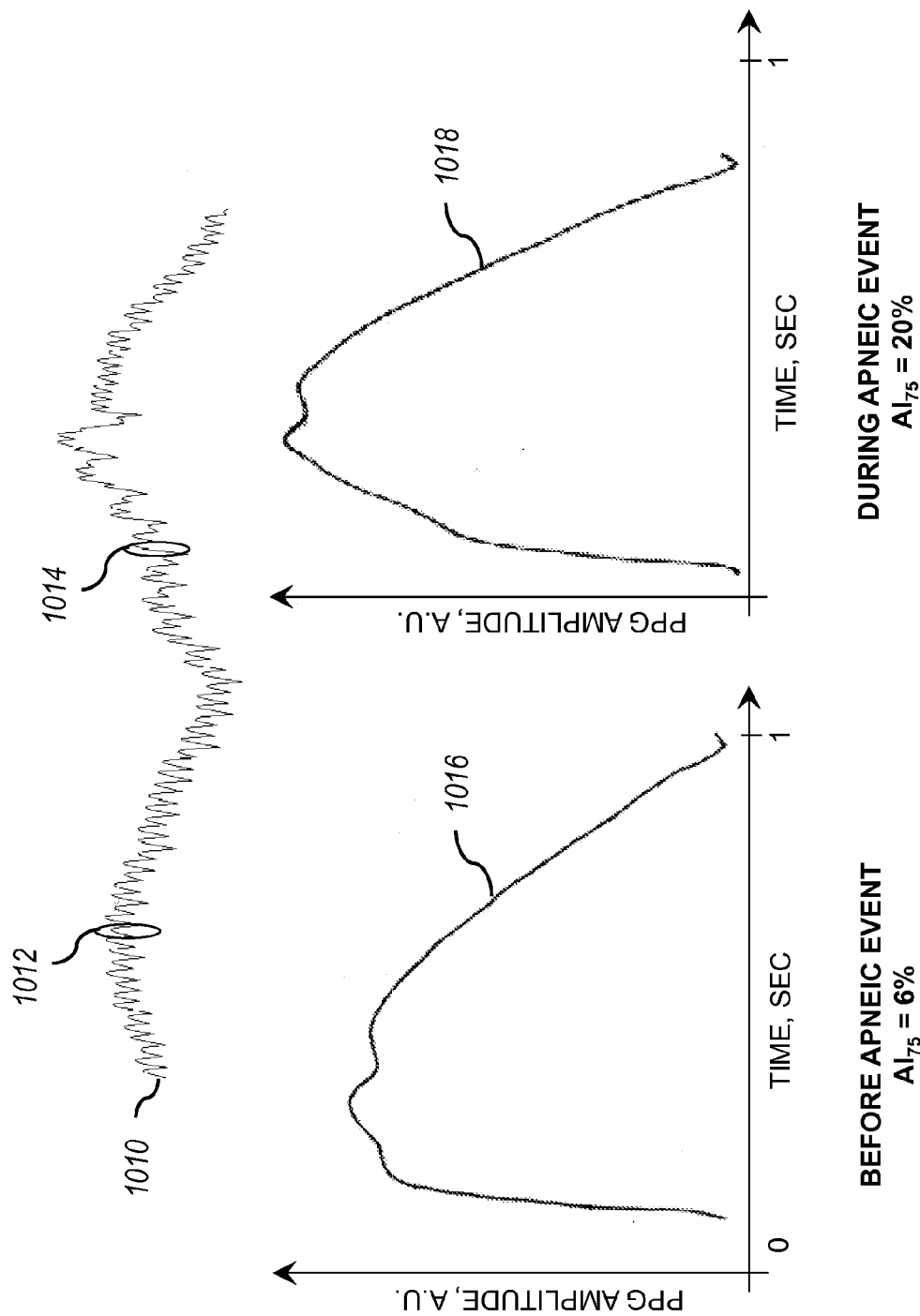
FIG. 10 is a timing diagram illustrating features of a photoplethysmography signal before and during an apneic episode with two pulse waves selected to demonstrate changes in vascular tone as assessed by an augmentation index.

At 904, the computer 234 may filter the PPG signal, for example, using a low pass filter or using a Fourier analysis to obtain PPG DC component before and during the apneic event. A line 1104*a* (FIG. 11*a*) is an illustrative example of applying at 904 a low pass filter (e.g., with a cutoff frequency of 0.3 Hz) to the signal of the line 1102a. With only filtering, the computer 234 determines, at 904, that a respiratory effort occurred. On the other hand, a line 1104b (FIG. 11b) is an illustrative example of applying at 904 a low pass filter (e.g., with a cutoff frequency of 0.3 Hz) to the signal of the line 1102b. With only filtering, the computer 234 does not determine, at 904, that a respiratory effort occurred. At 906, the computer 234 estimates vasoconstriction as a measure of the effect of the autonomous nervous system (ANS) on the DC component during the apneic event. At 907, the computer 234 computes a parameter describing vascular tone (e.g., augmentation index). In some embodiments, the computer 234 estimates the presence and the extent of sympathetically mediated vasoconstriction in the DC component, for example, by computing the augmentation index for each of the PPG pulse waves before and during an apneic event. The augmentation index is a measure of arterial stiffness and the arteries become stiffer as a result of sympathetically mediated vasoconstriction. Augmentation represents the difference between the second and first systolic peaks of the pulse waveform, and the augmentation index represents the augmentation expressed as a percentage of the pulse wave amplitude. The degree of an increase in augmentation index during an apneic event quantifies the effect of vasoconstriction on the DC component during the event. Since heart rate typically increases during an apneic event, a heart rate normalized measure of augmentation index yields a better estimate of the effect of vasoconstriction on the DC component of PPG signal. The effect of vasoconstriction on the PPG pulse waves before and during an apneic event is shown in FIG. 10, which is described in detail below. Other measures of arterial stiffening (such as pulse wave reflection index, etc.) and changes in vascular tone may be used to estimate the effect on the DC component. A line 1107a (FIG. 11a) and a line 1107b (FIG. 11b) are illustrative examples of computing, at 907, a parameter using an augmentation index (AI75) normalized to a heart rate of 75 beats per minute. At 908, the computer 234 performs a spectral analysis on the timing diagram of the AI75 to generate frequency intensities. The spectral analysis may be, for example, a Fourier analysis or a Hilbert analysis. At 909, the computer 234 scales the computed parameter based on the intensities of the frequencies identified in spectral analysis. A line 1109a (FIG. 11a) and a line 1109b (FIG. 11b) are illustrative examples of scaling, at 909, the computed parameter of lines 1107a and 1107b, respectively, with the spectral analysis at 909. In some embodiments, the data set of the PPG signal and the filtered PPG signal has a dimension that is different from the dimension of the data set of the computed parameters of the PPG pulses. For example, the PPG signal may be sampled at a frequency of 1,000 Hz to give 10,000 data points in a ten second period. The filtered PPG signal may have the same number of data points as the PPG signal. In contrast, the data set of the computer parameters may be 4-0 corresponding to 10 pulse waves during the ten second period. Also, the PPG signal and the filtered PPG signal may be measured as current corresponding to light absorption, while the computed parameter such as augmentation index, for example, may be computed as percentage. The computer 234 performs processing on the data sets to adjust the dimensions before scaling or after the scaling or both. At 910, once the effect of vasoconstriction has been estimated, the computer 234 subtracts the effect of the autonomous nervous system from the DC component to obtain, at 912, a measure of respiratory effort during the apneic event. A line 1112a (FIG. 11a) is an illustrative example of obtaining, at 912, the respiratory effort during time 1120a by subtracting the line 1109a from the line 1104a. Although the computer 234 did not detect the respiratory effort at 904 in the illustrative example of FIG. 11b, the computer 234 determines the respiratory effort at 912. A line 1112b (FIG. 11b) is an illustrative example of obtaining, at 912, the respiratory effort during time 1120b by subtracting the line 1109b from the line 1104b.

FIG. 10 is a timing diagram illustrating features of a photoplethysmography signal 1010 before and during an apneic episode with two pulse waves 1012 and 1014 selected to demonstrate changes in vascular tone as assessed by an augmentation index. A line 1016 represents the pulse wave 1012 for which the computer 234 calculates, at 902, an augmentation index ($AI_{75}$) of 6%. A line 1018 represents the pulse wave 1014 for which the computer 234 calculates, at 902, an augmentation index ($AI_{75}$) of 20%. The pulse 1012 occurs before the apneic event. The pulse 1018 occurs during the apneic event, and is reflective of more constricted state of the arteries than that represented by the pulse 1012.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise. Also, as used in the description herein and throughout the claims that follow, the meaning of "on" includes "in" and "on" unless the context clearly dictates otherwise.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the disclosure include process steps and instructions described herein in the form of an algorithm. It should be noted that the process steps and instructions of the disclosure could be embodied in software, firmware or hardware, and when embodied in software, could be downloaded to reside on and be operated from different platforms used by a variety of operating systems.

The disclosure also relates to an apparatus for performing the operations herein. This apparatus may be specially constructed for the required purposes, or it may comprise a general-purpose computer selectively activated or reconfigured by a computer program stored in the computer or in a non-transitory computer-readable media. Such a computer program may be stored in a computer readable storage medium (e.g., memory 214), such as, but is not limited to, a non-transitory electromagnetic medium such as a hard drive, a magnetic disk, a, magnetic-optical disk, an optical disk, a read-only memory (ROM), a random access memories (RAM), EPROM, EEPROM, magnetic or optical card, application specific integrated circuit (ASIC), a CD-ROM, a DVD, Blu-Ray, a flash memory, a USB memory card, a floppy disk, or any other medium from which a computer can read. Non-transitory computer-readable media comprise all computer-readable media except for a transitory, propagating signal. Furthermore, the computers and microcontrollers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description herein. In addition, the disclosure is not described with reference to any particular programming language. It will be appreciated that a variety of programming languages may be used to implement the teachings of the embodiments as described herein, and any references below to specific languages are provided for disclosure of enablement and best mode of the embodiments.

In addition, the language used in the specification has been principally selected for readability and instructional purposes, and may not have been selected to delineate or circumscribe the inventive subject matter. Accordingly, the disclosure is intended to be illustrative, but not limiting, of the scope of the invention, which is set forth in the claims.

What is claimed is:

1. A sleep monitoring device comprising:
   a housing including a region shaped to fit the contours of a patient's nose and configured to be disposed on the patient's face with said region to be disposed on said nose;
   at least one first sensor to sense physiological information related to the cardiovascular activity of the patient;
   a memory disposed in the housing and configured to store physiological information related to cardiovascular activity of the patient; and
   a processor disposed in the housing, coupled to the at least one first sensor, the processor configured to control the at least one first sensor and to control the memory to store physiological information related to cardiovascular activity of the patient,
   wherein the processor is further configured to obtain plethysmography data from the stored physiological information, to analyze a DC component of the plethysmography data, to detect changes in a DC component of the plethysmography data, to detect pulse waves in the plethysmography data, to calculate a measure of changes in vascular tone for each detected pulse wave, to adjust dimensions of the measure of the changes in vascular tone to match the detected changes of the DC component of plethysmography data, to scale spectral intensities of the measure of the changes in vascular tone to match the detected changes of the DC component of plethysmography data, and to subtract the adjusted measure of the changes in vascular tone from the DC component of the plethysmography data to obtain the respiratory effort.

2. A sleep monitoring device comprising:
   a housing including a region shaped to fit the contours of a patient's nose and configured to be disposed on the patient's face with said region to be disposed on said nose;
   at least one first sensor to sense physiological information related to the cardiovascular activity of the patient;
   a memory disposed in the housing and configured to store physiological information related to cardiovascular activity of the patient; and
   a processor disposed in the housing, coupled to the at least one first sensor, the processor configured to control the at least one first sensor and to control the memory to store physiological information related to cardiovascular activity of the patient, the processor further configured to:
   obtain plethysmography data from the stored physiological information; and identify respiratory effort by:
      detecting changes in a DC component of the plethysmography data,
      detecting pulse waves in the plethysmography data,
      calculating a measure of changes in vascular tone for each detected pulse wave, via an augmentation index determined by the difference between first and second systolic peaks of the pulse waveform,
      adjusting dimensions of the measure of the changes in vascular tone to match the detected changes of the DC component of plethysmography data,
      scaling spectral intensities of the adjusted measure of the changes in vascular tone to match the detected changes of the DC component of plethysmography data; and
      subtracting the scaled measure of the changes in vascular tone from the DC component of the plethysmography data to obtain the respiratory effort.

3. The sleep monitoring device according to claim 1 further comprising a second processor configured to analyze the physiological information related to the effects of an autonomous nervous system and respiratory effort on cardiovascular activity of the patient and determine respiratory effort of the patient based on the analyzed physiological information.

4. The sleep monitoring device according to claim 3 wherein the second processor is external to the housing.

5. The sleep monitoring device according to claim 3 wherein the second processor is disposed in the housing.

6. The sleep monitoring device according to claim 3 wherein the second processor is the first processor.

7. The sleep monitoring device according to claim 2 wherein the housing is shaped to fit the skin surface of the patient's nose and the area of maxillary sinuses.

8. The sleep monitoring device according to claim 2 wherein the housing further comprises an adhesive on a surface thereof configured to be continuously affixed to the patient during at least a monitoring period of the cardiovascular activity.

9. The sleep monitoring device according to claim 2 wherein the at least one sensor comprises a pair of photosensors that emit and measure absorption of light wavelengths typically absorbed by oxygenated and deoxygenated hemoglobin.

10. The sleep monitoring device according to claim 2 further comprising at least one second sensor to sense physiological information related to respiratory activity of the patient,
- wherein the memory is further configured to store physiological information related to respiratory activity of the patient;
- wherein the processor is coupled to the at least one second sensor, the processor is further configured to control the at least one second sensor and to control the memory to store physiological information related to respiratory activity of the patient.

11. The sleep monitoring device according to claim 1 further comprising an accelerometer positioned to detect the patient's movements and sleep time.

12. The sleep monitoring device according to claim 1 wherein the housing is shaped to fit the skin surface of the patient's nose and the area of maxillary sinuses.

13. The sleep monitoring device according to claim 1 wherein the housing further comprises an adhesive on a surface thereof configured to be continuously affixed to the patient during at least a monitoring period of the cardiovascular activity.

14. The sleep monitoring device according to claim 1 further comprising a power source configured to provide power during at least a monitoring period of the cardiovascular activity.

15. The sleep monitoring device according to claim 1 wherein the housing is made of a flexible bio-compatible material.

16. The sleep monitoring device according to claim 1 wherein the at least one sensor comprises a pair of photosensors that emit and measure absorption of light wavelengths typically absorbed by oxygenated and deoxygenated hemoglobin.

17. The sleep monitoring device according to claim 1 further comprising at least one second sensor to sense physiological information related to respiratory activity of the patient,
- wherein the memory is further configured to store physiological information related to respiratory activity of the patient;
- wherein the processor is coupled to the at least one second sensor, the processor is further configured to control the at least one second sensor and to control the memory to store physiological information related to respiratory activity of the patient.

18. The sleep monitoring device according to claim 17 wherein the at least one second sensor includes an airflow sensor to measure oronasal breathing.

19. The sleep monitoring device according to claim 17 wherein the at least one second sensor is an airflow sensor disposed in the housing, wherein the device further comprises tubing that protrudes from the housing and has an end mounted to the airflow sensor.

20. The sleep monitoring device according to claim 1 wherein the at least one first sensor comprises a photosensor that measures plethysmography data.

* * * * *